United States Patent [19]  [11] 4,336,388
Fryer et al.  [45] Jun. 22, 1982

[54] THIAZOLYL BENZOPHENONE COMPOUNDS

[75] Inventors: Rodney I. Fryer, North Caldwell; Norman W. Gilman, Wayne, both of N.J.

[73] Assignee: Hoffmann-La Roche Inc., Nutley, N.J.

[21] Appl. No.: 216,097

[22] Filed: Dec. 15, 1980

Related U.S. Application Data

[62] Division of Ser. No. 161,713, Jun. 23, 1980, Pat. No. 4,269,774.

[51] Int. Cl.³ .......................................... C07D 417/06
[52] U.S. Cl. .................................. 548/194; 548/204
[58] Field of Search ................................ 548/204, 194

[56] References Cited

U.S. PATENT DOCUMENTS 3,933,838  1/1976  Manghisi et al. ................... 548/194

Primary Examiner—Alton D. Rollins
Attorney, Agent, or Firm—Jon S. Saxe; Bernard S. Leon; Frank P. Hoffman

[57] ABSTRACT

There is presented compounds of formula

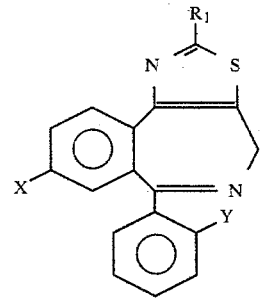

wherein X and Y are hydrogen or halogen and $R_1$ is lower alkyl or $NR_2R_3$
wherein $R_2$ and $R_3$ are hydrogen or lower alkyl
and the pharmaceutically acceptable salts thereof.

Also presented are novel intermediates and a process to produce the novel end products.

The compounds of formula I are useful as anxiolytic and sedative agents.

1 Claim, No Drawings

THIAZOLYL BENZOPHENONE COMPOUNDS

This is a division of application Ser. No. 161,713, filed June 23, 1980, now U.S. Pat. No. 4,269,774, issued May 26, 1981.

DESCRIPTION OF THE INVENTION

The present invention relates to compounds of the formula

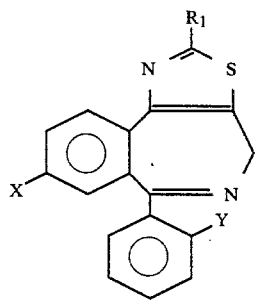

I wherein X and Y are hydrogen or halogen and $R_1$ is lower alkyl or $NR_2R_3$
wherein $R_2$ and $R_3$ are hydrogen or lower alkyl
and the pharmaceutically acceptable salts thereof.

As used herein, the term "halogen or halo" shall mean chloro, bromo and fluoro.

As used herein, the term "lower alkyl" shall mean a $C_1$ to $C_7$, preferably a $C_1$ to $C_4$, hydrocarbon radical which may be branched or straight chain, e.g., methyl, ethyl, isopropyl, butyl and the like.

The following reaction scheme sets forth a method to produce the compounds of formula I:

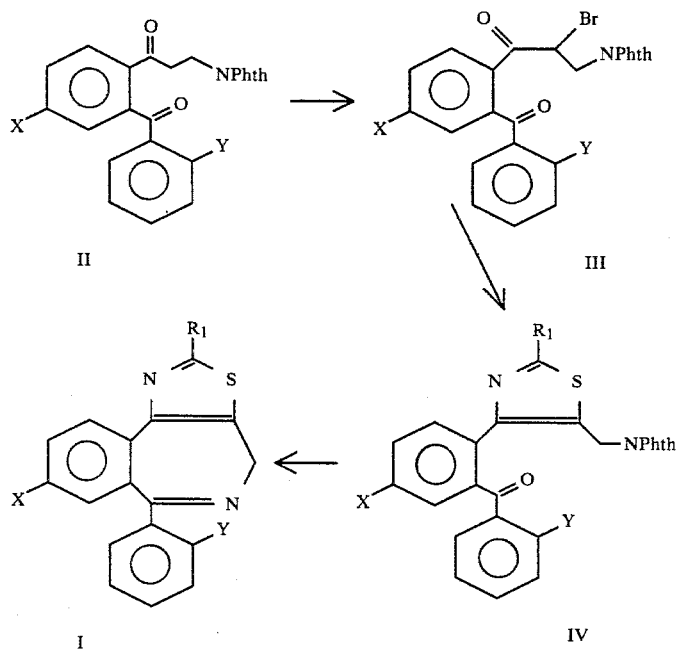

wherein $R_1$, X and Y are as above, and Phth stands for the phthaloyl moiety.

II→III

The compound of formula II is a known compound having been disclosed as a compound of formula VIII in U.S. application Ser. No. 10,118, now abandoned filed Feb. 7, 1979 together with a method for its production.

The compound of formula II is reacted with a brominating agent, such as, cuprous bromide or elemental bromine in acetic acid. Suitable solvents include inert organic solvents, such as, chlorinated hydrocarbons, e.g., methylene chloride or chloroform; ethers, e.g., tetrahydrofuran or dioxane or alkylacetates, e.g., ethyl or isopropyl acetate. When utilizing bromine in acetic acid, a solvent may be dispensed with.

The reaction may be run at from about room temperature to the reflux temperature of the selected solvent with reflux temperature as preferred.

III→IV

The compound of formula III is thereafter reacted with a substituted thioamide of the formula

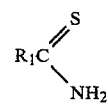

wherein $R_1$ is as above.

Suitable solvents include the inert organic solvents set forth in step II→III.

The reaction temperature may range from about room temperature to about 100° C. with about 90° C. as preferred.

Preferably sulfur dioxide is present in the solvent to prevent reduction of the intermediate (III) to the initial starting material (II).

IV→I

The compound of formula IV is thereafter reacted with an aqueous solution of a lower alkyl amine, e.g., methyl amine. A $C_1$ to $C_4$ alcohol is utilized as the solvent with ethanol as preferred. The reaction is most preferably carried out at about room temperature. The final product is isolated thereafter by utilizing well-known filtration techniques. The first formed open amine is not isolated but undergoes spontaneous ring closure to the final product I.

An alternate method to produce the compound of formula I consists of the reaction of the compound of formula IV with hydrazine in an inert solvent, such as, ethanol, a mixture of ethanol and chloroform, tetrahydrofuran or aqueous ethanol. The reaction temperature may vary from about room temperature to about 100° C. with reflux temperature of the selected solvent as preferred. The product is extracted with dilute mineral acid and thereafter recovered and neutralized.

A third method which may be utilized to produce the compound of formula I consists of a base followed by acid hydrolysis of the compound of formula IV. For the acid part of the hydrolysis, a 30% solution of a mineral acid, such as, hydrochloric, hydrobromic, sulfuric or phosphoric acid may be utilized. The reaction is run at or about reflux temperature. For a base part of the hydrolysis, an alkali metal hydroxide, such as, potassium or sodium hydroxide is utilized. Inert organic solvents, such as those set forth above, may be utilized to solubilize the ingredients. The reaction is run at or near reflux temperature of the selected solvent.

Compounds of formula I which are preferred are those wherein X and Y are halogen and $R_1$ is lower alkyl or amino, e.g., compounds of the formula:
8-chloro-6-(2-chlorophenyl)-2-methyl-4H-thiazolo[5,4-d][2]benzazepine, and
8-chloro-6-(2-fluorophenyl)-4H-thiazolo[5,4-d][2]benzazepin-2-amine.

The expression "pharmaceutically acceptable salts" is used to include salts with both inorganic and organic pharmaceutically acceptable strong acids, such as, sulfonic acid, hydrochloric acid, nitric acid, methanesulfonic acid and p-toluene sulfonic acid. Such salts can be formed quite readily by those skilled in the art with prior art and the nature of the compound to be place in salt form in view.

The thiazolo[5,4-d][2]benzazepines above are useful as pharmaceuticals and are characterized by activity as sedatives and anxiolytic agents. These compounds can be used in the form of conventional pharmaceutical preparations; for example, the aforesaid compounds can be mixed with conventional organic or inorganic, inert pharmaceutical carriers suitable for parenteral or enteral administration such as for example, water gelatin, lactose, starch, magnesium stearate, talc, vegetable oil, gums, polyalkylene glycols, Vaseline or the like. They can be administered in conventional pharmaceutical forms, e.g., solid forms, for example, tablets, dragees, capsules, suppositories or the like, or in liquid forms, for example, solutions, suspensions or emulsions. Moreover, the pharmaceutical compositions containing compounds of this invention can be subjected to conventional pharmaceutical expedients such as sterilization, and can contain conventional pharmaceutical excipients such as preservations, stabilizing agents, wetting agents, emulsifying agents, salts for the adjustment of osmotic pressure, or buffers. The compositions can also contain other therapeutically active materials.

A suitable pharmaceutical dosage unit can contain from about 1 to about 500 mg of the benzazepine end products with a dosage range of from 1 mg to about 100 mg being the preferred oral administration and a dosage range of from about 1 mg to about 50 mg being preferred for parenteral administration. However, for any particular subject, the specific dosage regimen should be adjusted according to individual need and the professional judgment of the person administering or supervising the administration of the aforesaid compounds. It is to be understood that the dosages set forth herein are exemplary only and that they do not, to any extent, limit the scope or practice of this invention.

The term "dosage unit" as employed throughout this specification refers to pharmaceutically discrete units suitable as unitary dosages for mammalian subject each containing a predetermined quantity of active material calculated to produce the desired therapeutic effect in association with the required pharmaceutical diluent, carrier or vehicle.

The following examples are illustrative, but not limitative of this invention. All temperatures given are in degrees centigrade, unless indicated otherwise.

EXAMPLE 1

2-{3-[(4-Chloro-2-chlorobenzoyl)phenyl]-3-oxopropyl}-1H-isoindole-1,3(2H)-dione

A stirred suspension of 1 g (0.01 mole) of mecuric sulfate in 55 ml of formic acid, 5 ml of water and 50 ml of methylene chloride was treated at room temperature over 5 minutes with 21.6 g (0.05 mole) of 1-[4-chloro-2-(2-chlorobenzoyl)phenyl]-3-(2-phthalimido)propyne. After stirring for 40 minutes, the mixture was poured into 250 ml of ice water, extracted with methylene chloride, dried over sodium sulfate and evaporated in vacuo. Crystallization of the residue from ethyl acetate in ether gave 20.8 g (92%). Recrystallization of a sample from 1:1 methanol/methylene chloride solution gave white prisms: mp 133°–134° C.

EXAMPLE 2

2-[3-(2-Benzoyl-4-chlorophenyl)-2-bromo-3-oxopropyl]-1H-isoindole-1,3(2H)-dione

A stirred mixture of 36 g (0.086 mole) of 2-[1-[4-chloro-2-(benzoyl)phenyl]oxopropyl]-1H-isoindole-1,3(2H)dione, 36 g (0.161 mole) of cupric bromide, 888 ml of tetrahydrofuran, 48 ml of ethyl acetate and 48 ml of chloroform was refluxed for 30 min, cooled, diluted with about 800 ml of methylene chloride and filtered. The green filtrate was washed with water, dried over sodium sulfate and concentrated at reduced pressure to give a yellow gum which crystallized from ether to give off-white crystals. Recrystallization of a sample from a 2:1 mixture of ethanol and methylene chloride gave white crystals: mp 136°–138° C.

EXAMPLE 3

2-[2-Bromo-3-[4-chloro-2-(2-fluorobenzoyl)phenyl]-3-oxopropyl]-1H-isoindole-1,3(2H)-dione This compound was prepared by the same procedure used in Example 2 using 19.2 g (0.044 mole) of 2-[[4-chloro-2-(2-fluorobenzoyl)phenyl]-3-oxopropyl]-1H-isoindole-1,3(2H)-dione 18 g (0.081 mole) of cupric bromide, 445 ml of tetrahydrofuran, 24 ml of ethyl acetate and 24 ml of chloroform. Off-white crystals were obtained. Recrystallization of a sample from 2:1 ethanol/methylene chloride solution gave white prisms: mp 125°–128° C.

EXAMPLE 4

2-[2-Bromo-3-[4-chloro-2-(2-chlorobenzoyl)phenyl]-3-oxopropyl]-1H-isoindole-1,3(2H)-dione This compound was prepared by the same procedure used in Example 2 using 16.5 g (0.037 mole) of the product obtained in Example 1, 15 g (0.067 mole) of cupric bromide, 370 ml of tetrahydrofuran, 20 ml of ethyl acetate and 20 ml of chloroform. Off-white crystals were obtained. Recrystallization of a sample from 1:1 methanol/methylene chloride solution gave white needles: mp 178°–179° C.

EXAMPLE 5

2-[4-[(2-Benzoyl-4-chlorophenyl)-2-methyl-5-thiazolyl]methyl]-1H-isoindole-1,3(2H)-diones A mixture of 7.5 g (0.015 mole) of the product obtained in Example 2, 2.25 g (0.03 mole) of thioacetamide and 105 ml of 10% sulfur dioxide in N,N-dimethylformamide solution was heated on a steam bath under drying tube for 1 hr. The reddish orange solution was poured over ice and the resulting reddish brown solid was collected by filtration, washed with water and air dried. Recrystallization of a sample from ethanol/methylene chloride solution gave off-white needles: mp 214°–216° C.

EXAMPLE 6

2-{[2-Amino-4-(2-benzoyl-4-chlorophenyl)-5-thiazolyl]methyl}-1H-isoindole-1,3(2H)-dione A stirred solution of 10 g (0.02 mole) of the end product of Example 2 and 2 g (0.026 mole) of thiourea in 60 ml of ethanol, protected by a drying tube, was refluxed for 1 hr. The yellow solution was poured over ice and diluted with water. The pale yellow solid was collected by filtration, washed with water and air dried on the funnel to give the end product. Recrystallization of a sample from methanol/methylene chloride solution gave pale yellow crystals: mp 253°–255° C.

EXAMPLE 7

2-{4-[4-Chloro-2-(2-chlorobenzoyl)phenyl-2-methyl]-5-thiazolyl-methyl}-1H-isoindole-1,3(2H)-dione This compound was prepared by the same procedure used for producing the compound of Example 5, using 3.2 g (0.006 mole) of the end product of Example 4, 0.9 g (0.012 mole) of thioacetamide and 42 ml of a 10% sulfur dioxide in N,N-dimethylformamide solution. The product was obtained as a reddish brown solid. Recrystallization of a sample from methanol/methylene chloride solution gave white needles: mp 238°–240° C.

EXAMPLE 8

2-{4-[4-Chloro-2-(2-fluorobenzoyl)phenyl-2-methyl-5-thiazolyl]methyl}-1H-isoindole-1,3(2H)-dione This compound was prepared by the same procedure used for producing the end product of Example 5 using 9 g (0.0175 mol) of the end product of Example 3, 2.7 g (0.036 mole) of thioacetamide and 135 ml of 10% sulfur dioxide in N,N-dimethylformamide solution to yield the end product. Recrystallization of a sample from ethanol/methylene chloride solution gave light tan needles: mp 228°–230° C.

EXAMPLE 9

2-{2-Amino-4-[4-chloro-2-(2-fluorobenzoyl)phenyl-5-thiazolyl]methyl}-1H-isoindole-1,3(2H)-dione This compound was prepared by the same procedure used in Example 6, using 7 g (0.014 mole) of the end product of Example 3, 1.4 g (0.018 mole) of thiourea and 42 ml of ethanol. The crude product was obtained as a pale yellow solid. Recrystallization of a sample from ethanol/methylene chloride solution gave yellow needles: mp 246°–248° C.

EXAMPLE 10

2-{2-Amino-4-[4-chloro-2-(2-chlorobenzoyl)phenyl-5-thiazolyl]methyl}-1H-isoindole-1,3(2H)-dione, 0.3 molar methylene chloride solvate This compound was prepared by the same procedure used in Example 6, using 3.2 g (0.006 mole) of the end product of Example 4, 0.6 g (0.0078 mole) of thiourea and 40 ml of ethanol. The crude product was obtained as a pale yellow solid. Recrystallization from methanol/methylene chloride solution gave yellow prisms: mp 238°–240° C.

EXAMPLE 11

8-Chloro-2-methyl-6-phenyl-4H-thiazolo[5,4-d][2]benzazepine

A mixture of 6.7 g (0.014 mole) of the end product of Example 5, 56 ml of 40% aqueous methyl amine solution and 80 ml of ethanol was stirred at room temperature for 2 hrs. The dark solution was evaporated in vacuo and the residue was partitioned between methylene chloride and water. The organic phase was dried over sodium sulfate and concentrated in vacuo. The residue was stirred with boiling ether, cooled and filtered. Evaporation of the filtrate gave a dark gum which was filtered over silica gel using a solution of 2% ethyl acetate in methylene chloride, followed by 5% ethyl acetate in methylene chloride. Evaporation of the latter fractions gave a dark oil which crystallized on standing. Recrystallization from ether/petroleum ether solution gave tan crystals. A second recrystallization of a sample gave off-white prisms: mp 128°–130° C.

EXAMPLE 12

8-Chloro-6-phenyl-4H-thiazole[5,4-d][2]benzazepin-2-amine

A mixture of 6 g (0.0127 mole) of the end product of Example 6, 120 ml of a 40% aqueous solution of methylamine and 180 ml of ethanol was stirred at room temperature for 1.5 hr. Evaporation in vacuo gave a gum which crystallized from a small amount of methanol to give tan crystals. Recrystallization of a sample from ethanol/methylene chloride solution gave pale yellow prisms: mp 244°–246° C. (dec.)

EXAMPLE 13

8-Chloro-6-(2-chlorophenyl)-2-methyl-4H-thiazolo[5,4-d][2]benzazepine

This compound was prepared by the same procedure as Example 11, using 2.9 g (0.0057 mole) of the end product of Example 7, 60 ml of a 40% aqueous methylamine solution and 90 ml of ethanol. During evaporation of the reaction mixture, an off-white solid separated. The solid was collected by filtration, washed successively with ethanol and petroleum ether and air dried. Recrystallization of a sample from ethyl acetate gave off-white prisms: mp 162°–164° C.

EXAMPLE 14

8-Chloro-6-(2-fluorophenyl)-2-methyl-4H-thiazolo[5,4-d][2]benzazepine

This compound was prepared using the same procedure as Example 11, using 8 g (0.0163 mole) of the end product of Example 8, 65 ml of a 40% aqueous solution of methylamine and 100 ml of ethanol. The end product was off-white prisms after filtration over silica gel and recrystallization from ether/petroleum ether solution (charcoal): mp 147°–149° C.

EXAMPLE 15

8-Chloro-6-(2-fluorophenyl)-4H-thiazolo[5,4-d][2]benzazepin-2-amine

This compound was prepared by the same procedure as Example 12, using 6.4 g (0.013 mole) of the end product of Example 9, 55 ml of a 40% aqueous solution of methylamine and 80 ml of ethanol. The purified product was crystallized from ether. Recrystallization of a sample from methanol/methylene chloride solution gave pale yellow prisms: mp 248°–250° C. (dec.).

EXAMPLE 16

8-Chloro-6-(2-chlorophenyl)-4H-thiazolo[5,4-d][2]benzazepin-2-amine

This compound was prepared by the same procedure as Example 12, using 1.2 g (0.0024 mole) of the end product of Example 10, 24 ml of a 40% solution of aqueous methylamine and 36 ml of ethanol. The crude product was recrystallized from methanol/methylene chloride solution to give pale yellow prisms: mp 255°–257° C. (dec.).

EXAMPLE 17

| Item | Ingredients | TABLET FORMULATION (Wet granulation) | | | |
|---|---|---|---|---|---|
| | | mg/tablet | mg/tablet | mg/tablet | mg/tablet |
| 1. | 8-chloro-6-(2-fluorophenyl)-4H-thiazolo[5,4-d][2]benzazepin-2-amine 8-chloro-6-(2-chlorophenyl)-2-methyl-4H-thiazolo[5,4-d][2]benzazepine | 1 | 5 | 10 | 25 |
| 2. | Lactose | 202 | 232 | 261 | 280 |
| 3. | Modified Starch | 25 | 35 | 45 | 55 |
| 4. | Pregelatinized Starch | 20 | 25 | 30 | 35 |
| 5. | Distilled water q.s. | — | — | — | — |
| 6. | Magnesium Stearate | 2 | 3 | 4 | 5 |
| | Weight of tablet | 250 mg | 300 mg | 350 mg | 400 mg |

Procedure:
1. Mix Items 1–4 in a suitable mixer.
2. Granulate with sufficient distilled water to proper consistency. Mill.
3. Dry in a suitable oven.
4. Mill and mix with magnesium stearate for 3 minutes.
5. Compress on a suitable press equipped with appropriate punches.

EXAMPLE 18

| Item | Ingredients | TABLET FORMULATION (Direct compression) | | | |
|---|---|---|---|---|---|
| | | mg/tablet | mg/tablet | mg/tablet | mg/tablet |
| 1. | 8-chloro-6-(2-fluorophenyl)-4H-thiazolo[5,4-d][2]benzazepin-2-amine 8-chloro-6-(2-chlorophenyl)-2-methyl-4H-thiazolo[5,4-d][2]benzazepine | 1 | 5 | 10 | 25 |
| 2. | Lactose | 221 | 217 | 212 | 181 |
| 3. | Avicel | 45 | 45 | 45 | 55 |
| 4. | Direct Compression Starch | 30 | 30 | 30 | 35 |
| 5. | Magnesium Stearate | 3 | 3 | 3 | 4 |
| | Weight of tablet | 300 mg | 300 mg | 300 mg | 300 mg |

Procedure:
1. Mix Item 1 with an equal amount of lactose. Mix well.
2. Mix with Items 3 and 4, and the remaining amount of Item 2. Mix well.
3. Add magnesium stearate and mix for 3 minutes.
4. Compress on a suitable press equipped with appropriate punches.

EXAMPLE 19

| Item | Ingredients | CAPSULE FORMULATION | | | |
|---|---|---|---|---|---|
| | | mg/tablet | mg/tablet | mg/tablet | mg/tablet |
| 1. | 8-chloro-6-(2-fluorophenyl)-4H-thiazolo[5,4-d][2]benzazepin-2-amine 8-chloro-6-(2-chlorophenyl)- | 1 | 5 | 10 | 25 |

-continued

CAPSULE FORMULATION

| Item | Ingredients | mg/tablet | mg/tablet | mg/tablet | mg/tablet |
|---|---|---|---|---|---|
| | 2-methyl-4H-thiazolo[5,4-d]-[2]benzazepine | | | | |
| 2. | Lactose | 203 | 293.5 | 328 | 372.5 |
| 3. | Starch | 30 | 35 | 40 | 30 |
| 4. | Talc | 15 | 15 | 20 | 20 |
| 5. | Aerosol OT | 1 | 1.5 | 2 | 2.5 |
| | Capsule fill weight | 250 mg | 350 mg | 400 mg | 450 mg |

Procedure:
1. Mill Items 1, 2, 3 and 5 in a suitable mixer. Mill.
2. Add talc and mix well.
3. Encapsulate on suitable equipment.

What is claimed:
1. A compound of the formula

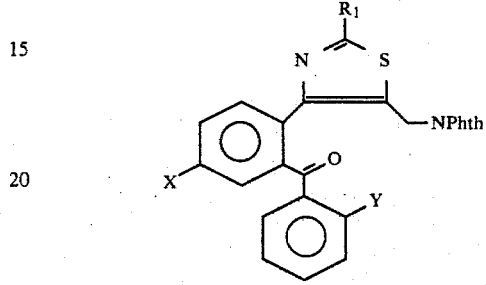

wherein X and Y are hydrogen or halogen, $R_1$ is lower alkyl or $NR_2R_3$
wherein $R_2$ and $R_3$ are hydrogen or lower alkyl and Phth is phthaloyl.

* * * * *